United States Patent [19]
Seliger et al.

[11] Patent Number: 5,574,141
[45] Date of Patent: Nov. 12, 1996

[54] FUNCTIONALIZED CARRIER MATERIALS FOR THE SIMULTANEOUS SYNTHESIS AND DIRECT LABELING OF OLIGONUCLEOTIDES AS PRIMERS FOR TEMPLATE-DEPENDENT ENZYMATIC NUCLEIC ACID SYNTHESES

[75] Inventors: Hartmut Seliger, Elchingen, Germany; Wojciech Markiewicz, Poznan, Poland; Gabriele Gröger, Elchingen, Germany; Rudi Rösch, Ulm, Germany; Margit Klotz, Schelklingen, Germany

[73] Assignee: Boehringer Mannheim GmbH, Mannheim, Germany

[21] Appl. No.: 199,248

[22] PCT Filed: Aug. 22, 1992

[86] PCT No.: PCT/EP92/01932

§ 371 Date: Feb. 28, 1994

§ 102(e) Date: Feb. 28, 1994

[87] PCT Pub. No.: WO93/05060

PCT Pub. Date: Mar. 18, 1993

[30]  Foreign Application Priority Data

Aug. 28, 1991 [DE] Germany .......................... 41 28 480.1

[51] Int. Cl.$^6$ .......................... C07H 19/00; C07H 21/00; C12P 19/34; C12Q 1/68
[52] U.S. Cl. ...................... 536/22.1; 536/25.3; 435/91.1; 435/91.2; 435/6; 435/5
[58] Field of Search ................................. 536/25.3, 22.1; 526/336; 501/33; 435/91.1, 91.2, 6, 91.5

[56]  References Cited

U.S. PATENT DOCUMENTS

| | | | |
|---|---|---|---|
| 5,082,934 | 1/1992 | Saba et al. | 536/17.6 |
| 5,141,813 | 8/1992 | Nelson et al. | 428/402 |
| 5,401,837 | 3/1995 | Nelson et al. | 536/25.36 |
| 5,403,709 | 4/1995 | Agrawal et al. | 435/6 |

FOREIGN PATENT DOCUMENTS

| | | |
|---|---|---|
| 0325970 | 8/1989 | European Pat. Off. . |
| 0423839A3 | 4/1991 | European Pat. Off. . |
| 0200362B1 | 1/1993 | European Pat. Off. . |
| 666183 | 6/1979 | U.S.S.R. . |
| 1318600 | 5/1987 | U.S.S.R. . |
| 1439108 | 11/1988 | U.S.S.R. . |

OTHER PUBLICATIONS

Murasugi et al., DNA, "Blotin–Labeled Oligonucleotides: Enzymatic Synthesis and Use as Hybridization Probes", vol. 3, No. 3, 269–277 1994.

Ortigao et al., Nucleosides & Nucleotides, "5–Bromouridinylated Oligonucleotides for Hybridization Analysis of DNA and RNA on Membranes and in Situ", vol. 8, (5&6), 805–813 (1989).

Sanger et al., Proc. Natl. Acad. Sci. USA, "DNA Sequencing with chain–terminating inhibitors", vol. 74, No. 12, pp. 5463–5467, Dec. 1977.

Cook et al., "—and hybridization of a series biotinylated oligonucleotides", Nov. 1988, vol. 136: pp. 4077–4095.

Kessler et al., "Non–radioactive Labeling and Detection of Nucleic Acids", vol. 371, pp. 917–927, Oct. 1990.

Seliger et al., Nucleosides & Nucleotides "Specific intrachain introduction of reporter groups into oligonucleotides as substituents at internuceotidic linkages", 10 (1–3), 303–306 (1991).

Aleksandrova et al., Mol Biol (MOSC), "Fluorescent Analogues of Nucleoside 5'Triphosphates for . . . ", vol. 24, (4) 1990, 1100–1108 abstract only.

Wachter et al., Nucleic Acids Research, "A simple and efficient procedure for the synthesis of 5'–aminoalkyl oligodeoxynucleotides", Nucleic Acids Res. vol. 14, No. 20, pp. 7985–7994, 1986.

Connolly, Nucleic Acids Research, "The synthesis of oligonucleotides containing a primary amino group at the 5'–terminus", vol. 15, No. 17, 3131–3139 1987.

MacMillan et al., J. Org. Chem, "Synthesis of Functionally Tethered Oligodeoxynucleotides by the Convertible Nucleoside Approach", vol. 55, 1990, pp. 5931–5933.

Pieles et al., Nucleic Acids Research, "A protected biotin containing deoxycytidine building block for solid phase synthesis of biotinylated oligonucleotides", vol. 18, No. 15, 4355–4360, 1990.

Levenson et al., 3–Biochem. Genetics, "Nonisotopically labeled probes and primers", vol. 112, p. 209 1990.

Agrawal et al., Nucleic Acids Research, "Efficient methods for attaching non–radioactive labels to 5' ends of synthetic oligodeoxyribonucleotides", vol. 14, No. 15, pp. 6227–6245 1986.

Dattagupta et al. EPA–0527433–(Miles Inc.) Novel Fluorescent Label, pp. 1–16 Jun. 8, 1992.

Kessler et al, Nonradioactive labeling and detection of nucleic acids, Chem Hoppe Seyler, vol. 371: pp. 917–927 Oct. 1990.

Primary Examiner—W. Gary Jones
Assistant Examiner—Dianne Rees
Attorney, Agent, or Firm—Nikaido, Marmelstein, Murray & Oram LLP

[57]  ABSTRACT

The synthesis and use of polymeric carriers is described which are loaded with nucleic acid building blocks which in turn contain labelling groups or precursors thereof. The polymeric carrier loaded in this way serves as a solid or liquid phase for the assembly of oligonucleotides which can be used as primers for template-dependent enzymatic nucleic acid syntheses such as for example in sequencing analysis according to Sanger and co-workers or in the polymerase chain reaction (PCR).

14 Claims, 13 Drawing Sheets

FUNCTIONALIZED CARRIER MATERIALS FOR THE SIMULTANEOUS SYNTHESIS AND DIRECT LABELING OF OLIGONUCLEOTIDES AS PRIMERS FOR TEMPLATE-DEPENDENT ENZYMATIC NUCLEIC ACID SYNTHESES

This application is a 371 of PCT/EP92/01932, filed Aug. 22, 1992.

Techniques for the hybridization of nucleic acid fragments to DNA or RNA and their template-dependent enzymatic extension coupled with their non-radioactive labelling, e.g. by fluorescent dyes or affinity groups, are the basis for many applications of oligonucleotides in the biomedical field. These include for example the sequencing of nucleic acids by means of labelled primers according to Sanger's dideoxy method or the use of the polymerase chain reaction (PCR) in connection with nucleic acid diagnostics. Non-radioactive labelling methods should generally be preferred for such purposes since this approach avoids problems of handling of and contamination with radioisotopes as well as the difficulties in their storage and disposal.

The introduction of non-radioactive labelling groups can in principle be achieved by chemical or enzymatic means. In this connection one has to assume that the synthesis of the oligonucleotide chains themselves is usually carried out by chemical means. Therefore a subsequent enzymatic labelling, e.g. by reacting oligonucleotides with 5-bromo-dUTP (Nucleosides & Nucleotides 8, 805–813 (1989)), biotin-dUTP (Nucleic Acids Res. 16, 4077–4095 (1988)) or digoxigenin-dUTP (Biol. Chem. Hoppe Seyler 371, 917–927 (1990)) catalysed by deoxynucleotidyl-terminal transferase is from the outset complicated by the necessity for additional process steps. Above all, it should, however, be noted that this is usually an extension with structurally modified nucleoside-5' triphosphates beyond the 3' end of the oligonucleotide chain. In this process more than one nucleotide unit is usually (depending on the template) attached automatically to the 3' end, so that oligonucleotides labelled in this way cannot be used from the outset for all template-dependent chain extensions.

Deoxyoligonucleotides can be non-radioactively labelled by chemical means by introducing appropriate groups either on the nucleobase, on the sugar residue or at the internucleotide bond (phosphate). At present this is almost exclusively carried out during or after synthesis and processing of the oligonucleotide. In this way one either substitutes the 5'-OH end of the oligonucleotide chain (Nucleic Acid Res. 14, 6227–6245 (1986); Nucleic Acids Res. 14, 7985–7994 (1986)), nucleobases at the 5' end or internal (Nucleic Acids Res. 15, 3131–3139, (1987); J. Org. Chem. 55, 5931–5933, (1990)) or 5'-terminal (Nucleic Acids Res. 18, 4355–4360 (1990)) or internucleotidic (Nucleosides & Nucleotides 10, 303–306 (1991)) phosphate groups. Most labelling reactions are carried out by reactions after chemical synthesis of the chain. In this case the reaction partner is the relatively labile oligonucleotide chain so that there is a considerable risk of side reactions. In some cases labelling groups are introduced in such a way that appropriate amidophosphite derivatives are used as reagents. Such reagents are usually less stable and can only be stored in solution for a limited period. Recently CPG carrier materials have been described which enable the introduction of groups at the 3'-OH end of an oligonucleotide chain (Belmont, Calif., p. 188).

However, the 3'-OH end is blocked by these groups against any further chain extension so that oligonucleotides labelled in this manner do not come into consideration as primers for template-dependent polymerase reactions. Up to now 5'-terminally labelled oligonucleotides have been used exclusively for all oligonucleotides which have been used for template-dependent polymerase reactions. In this case it has been assumed that, on the one hand, internal labelling groups can interfere with the hybridization and, on the other hand, that template-dependent polymerases do not extend a primer beyond the 3' end if this contains a non-biological substituent at this position.

Surprisingly we have now found that deoxyoligonucleotides are also accepted as primers by DNA polymerases and are incorporated into polynucleotides even when they contain labelling groups, such as fluorescent dyes at the 3'-terminal base. In this case they are incorporated with the same efficiency as a primer provided with a 5'-terminal labelling group. We have developed a preferred process on the basis of this finding which enables oligonucleotide sequences to be obtained and used in a labelled form without the need to use amidophosphite derivatives provided with appropriate functional groups either during or after the oligonucleotide synthesis.

The invention therefore concerns a mononucleoside modified by means of a labelling group which is bound to a polymeric carrier, its use for the synthesis of terminally-labelled oligonucleotides as well as the use of these oligonucleotides as primers for polymerase-catalysed chain extension.

The invention is based on the production and use of labelling phases as solid or also liquid phases for chemical oligonucleotide synthesis.

Labelling phases are understood as polymeric carriers which, as described below, by means of the type of their functionalization attach one or several substituents to the beginning of an oligonucleotide chain which are themselves labelling groups or precursors of the same. The substituents are attached in such a way that after the oligonucleotide synthesis and cleavage of the oligonucleotide from the labelling phase, it's 3'-OH group is free for template-dependent chain extension with polymerases. Carrier materials in this case are any desired non-cross-linked or cross-linked polymers, as well as organic or inorganic materials, preferably polystyrene derivatives, silica gel or controlled pore glass or even soluble derivatives of polyethylene glycol which can be linked to a nucleoside or nucleotide (preferably via a spacer) by the presence of suitable anchor groups, such as those carriers which are common for chemical oligonucleotide synthesis.

Labelling phases within the meaning of our invention is used to denote carrier materials of the above-mentioned type which are linked via a non-nucleosidic spacer to a nucleoside or nucleotide or a derivative or a precursor thereof provided with a labelling group. Mononucleosides are preferred in this case.

Non-nucleosidic spacers which can be used are the usual linkers in chemical oligonucletide synthesis for linking nucleosides and nucleotides and carrier materials such as e.g. the "long chain alkylamine" spacer (Oligonucleotide, Synthesis, A practical approach; M. J. Gait, IRL Press 1984 Oxford).

An anchor group within the meaning of the invention is a chemical group of the carrier to which other chemical compounds can be covalently bound in aqueous medium or in organic solvents. Preferred anchor groups are amino groups, the hydroxyl group or the mercapto group. $NH_2$ is particularly preferred.

The term labelling groups denote all substituents linked covalently and, if desired linked via a spacer, to the nucleoside anchored to the labelling phase which are able to impart a particular structural property to the oligonucleotide synthesized on this solid or liquid phase which is not inherent to the oligonucleotide chain itself. Non-radioactive labelling groups are preferred. These are preferably fluorescent, luminescent, antigenic or affinity-mediating groups and complex-forming groups. Furthermore these are also understood to include those groups, e.g. amino groups, which enable the attachment of a label, if necessary in a protected form. In a wider sense, those groups which as substituents of an oligonucleotide chain for example enable a possible therapeutic application of oligonucleotides by their capability of specifically binding or cleaving DNA or RNA [or proteins] should also be designated labelling groups within the scope of the invention. Particularly preferred labelling groups are haptens such as fluorescein, digoxigenin and biotin. Haptens are immunologically reactive chemical compounds with a molecular weight of less than 500 g/mol which do not themselves trigger an immune response but do so after coupling to a macromolecular carrier.

Oligonucleotides within the sense of our invention are understood as sequences which are composed of biological nucleotide units as well as those which are composed entirely or partially of building blocks which are structurally modified compared to biological DNA or RNA and/or modified internucleotide bonds.

By use of the labelling phases it is also possible to produce the oligonucleotides according to the invention in automated processes according to methods known in the literature and using synthons known in the literature. This does not exclude the case that analogous to methods known in the literature further labelling groups of the same or another type are likewise introduced during the synthesis at any other desired positions in the oligonucleotide chain in addition to those introduced by means of the labelling phase. However, the oligonucleotides synthesized on the labelling phase can even only be the usual biological nucleic acid building blocks.

The oligonucleotides are preferably synthesized from the 3' to the 5' end of the desired sequence. When using appropriate synthons (see example), the synthesis can also alternatively be carried out on any desired carriers from the 5' to the 3' end in which one or several nucleosides are used at the 3'-terminus the nucleobase of which is substituted with a labelling group within the meaning of our invention.

In order to produce the oligonucleotides according to the invention, the carrier material with the anchor group which is preferably an amino group is reacted with a mononucleoside which is preferably activated at the 3' hydroxyl group and protected in the usual manner on the other reactive groups (e.g. 5' OH and primary amino groups of the nucleobases). This mononucleoside preferably has either a spacer with a terminal labelling group, preferably a reactive and protected group, on an amino group of the base or on an additional substituent attached to the base.

If this nucleoside contains a group on the base which does not occur in the other mononucleoside units of the oligonucleotide to be synthesized, it is possible to selectively label the completed oligonucleotide at this base.

Subsequently the 5'-O-protecting groups (e.g. dimethoxytrityl) are cleaved from the labelling phase produced in this manner which preferably contains the protected mononucleoside bound via a spacer to the carrier material. Subsequently an oligonucleotide synthesis known from the state of the art is carried out on the labelling phase preferably by the solid phase method via coupling of nucleotide building blocks via phosphoramidites until the desired nucleotide sequence is achieved.

After the synthesis, the labelled oligonucleotide chains are freed of protecting groups if necessary and cleaved from the polymers in such a way that the labelling groups or their precursors remain at the 3' end of the oligonucleotide chain (and also at other positions if they were attached there).

If the labelling phase only contains a precursor of the labelling group or if only a precursor of a labelling group was introduced during the synthesis at the 3' position, this must be converted into the actual labelling group in a subsequent step.

Oligonucleotides labelled within the meaning of our invention at the 3' terminus can be used as primers in template-dependent polymerisations catalysed by DNA or RNA polymerases. The usual reaction conditions described in the literature for the various variants of template-dependent polymerase reactions can be used for this (e.g. EP-A 0 200 362).

For example it was possible to use primers which were labelled according to the invention with fluorescein at the 3' position for the sequence analysis of single-stranded DNA. The sequencing can be carried out according to the dideoxy method of F. Sanger et al. (Proc. Natl. Acad. Sci. USA 74, 5463–5467 (1977)) in accordance with the working instructions of the Pharmacia Company (Pharmacia-LKB Autoprimer™ Synthesis Kit (27-9290-01)). In this way it was possible according to example 4 to read sequences up to ca. 500 bases of pUC19-DNA as well as in octopus DNA D3.

The sequencing of M13mp18 is described in example 5 which similarly leads to the reading of correspondingly longer sequences.

For example sections of 141 and 145 bases of the double-stranded M13mp18RF DNA could be amplified according to instructions known from the literature by using the oligonucleotide primer described in example 6 (together with a non-labelled reverse primer) each labelled with fluorescein at the 3' position. After gel electrophoresis, the amplified DNA fragments were visualized by ethidium bromide staining. The presence of fluorescein residues was detected fluorometrically.

The use of labelling phases to obtain labelled oligonucleotides within the meaning of the invention is of particular advantage in as much that these phases not only enable the synthesis of oligonucleotides as solid or liquid phases for the purposes of the Merrifield synthesis but also at the same time have the character of stable labelling reagents. It is therefore unnecessary to use other labelling reagents which have previously had to be employed during or after the oligonucleotide synthesis.

Such labelling reagents often only have a limited stability in particular when they are amidophosphite reagents. In addition it is especially advantageous that when labelling phases are used it is possible to routinely carry out the actual synthesis of the oligonucleotide chain in automated methods without the requirement for additional reagents or synthetic steps. The essential, if not all, steps which are necessary to introduce the labelling groups are thus transferred to before the start of the oligonucleotide synthesis.

Thus with one batch of a labelling phase it is possible to produce a variety of numerous desired sequences which have the appropriate labelled nucleoside (or several appropriate nucleosides) as the 3'-terminus. In contrast it has previously been necessary to label each individual oligonucleotide separately from e.g. a series of sequencing primers or amplimers for PCR diagnostics. The use of labelling phases and the 3'-labelled oligonucleotides obtained thereby thus enables a rationalization of all those methods which are based on template-dependent polymerase reactions using 3'-terminally labelled oligonucleotides as primers, in particular the sequencing reactions according to Sanger or PCR.

This is a result of the fact that at least n labelling reactions or labelling steps are no longer necessary to non-radioactively label a set of n sequencing primers but instead only four labelling phases. If wobble pairings are utilized (I with T and C, U with A and G) the requirement is reduced to two labelling phases. If the remaining requirement for labelling reactions during the production of the labelling phases is taken into account then the work required for the labelling of oligonucleotides is thus reduced to ca. 2/n to 4/n. This means that for example 96–98% of the labelling work can be saved for the production of a set of ca. 100 primers of different sequences. If for example 1000 primers are necessary for a large sequencing procedure then the savings even increase to 99.6–99.8% etc.

The invention is elucidated in more detail by the following examples.

EXAMPLE 1

Figure 1:
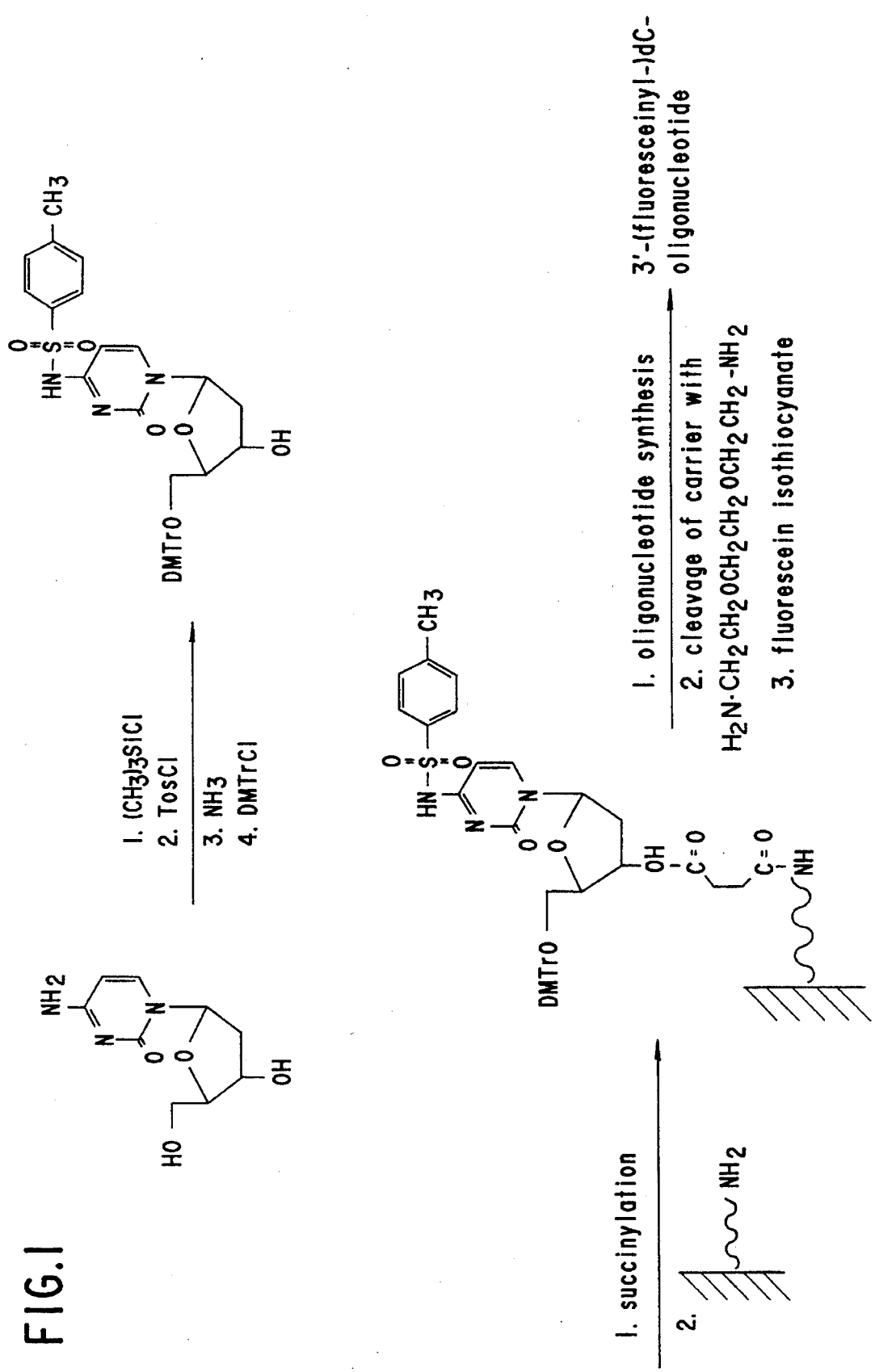
FIG. 1 shows the synthesis of a deoxycytidine carrier modified with tosyl, the release of the modified oligonucleotide and reaction with a reporter group (in this case fluorescein).
Figure 2:
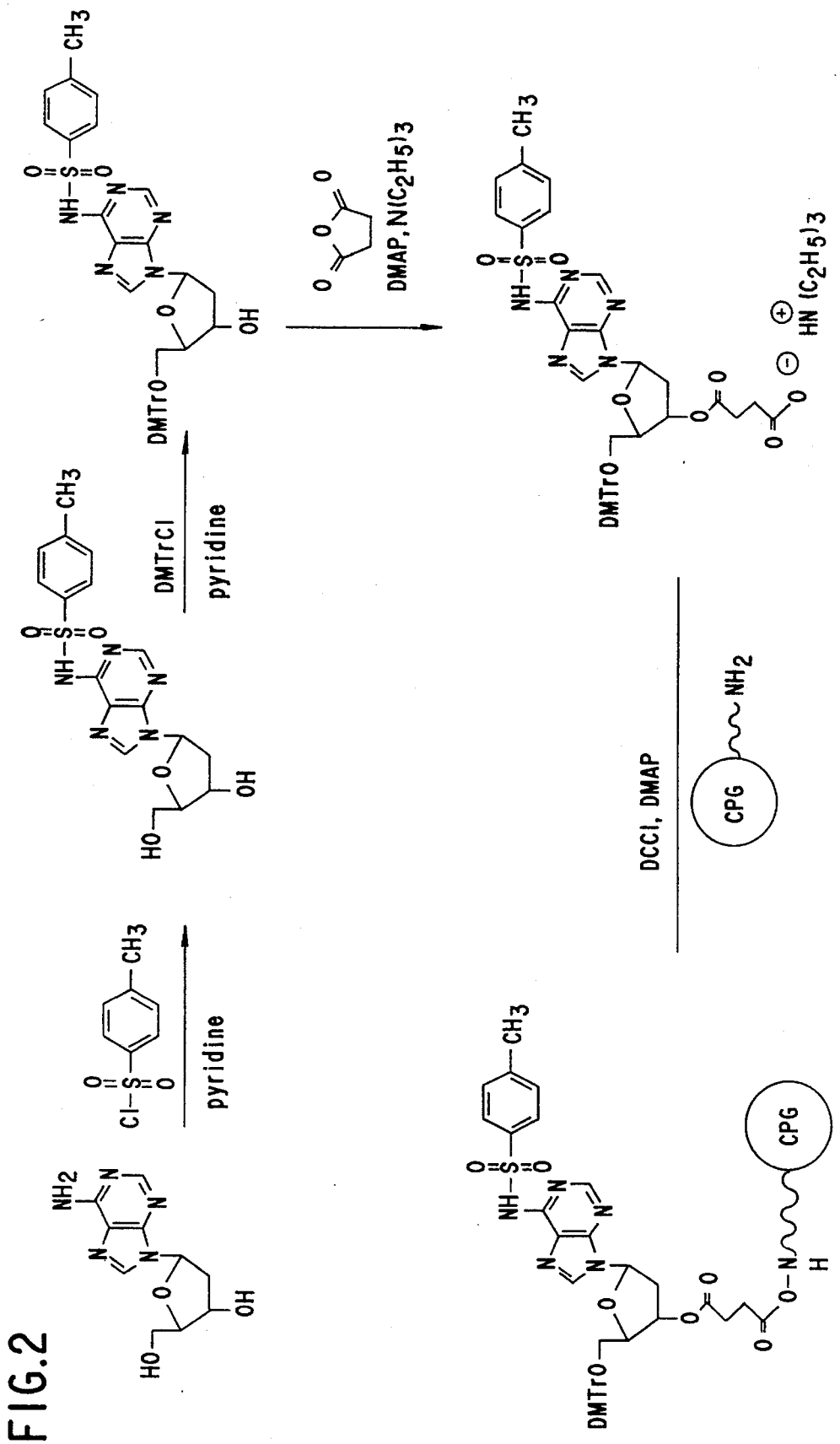
FIG. 2 shows the same procedure for deoxyadenosine and deoxyguanosine.

Synthesis of Protected, Labelled Nucleosides for Obtaining Labelling Phases a) Deoxycytidine carrier (FIG. 1)
aa) Synthesis of 5'-O-dimethoxytrityl-4-N-p-toluenesulfonyl-2'-deoxycytidine 2'-deoxycytidine hydrochloride (1.32 g, 5 mmol) is allowed to react for 1 hour with trimethylsilyl chloride (2.5 ml, 20 mmol) in anhydrous pyridine (20 ml) while stirring. The reaction mixture is then concentrated by evaporation to a volume of ca. 15 ml while excluding moisture and p-toluenesulfonyl chloride (1.9 g, 10 mmol) is added. The well-sealed reaction vessel is stored overnight at 60° C. in a drying cupboard. Examination of the mixture by thin-layer chromatography shows a complete conversion of the starting materials. The reaction volume is increased by addition of dichloromethane (50 ml) and the organic phase is extracted by shaking with a saturated aqueous sodium bicarbonate solution (60 ml). The aqueous layer is extracted twice with dichloromethane (20 ml). The combined extracts are concentrated in a water jet vacuum and made up to a volume of ca. 15 ml with pyridine. Concentrated aqueous ammonia solution (15 ml) is added to this and the progress of the desilylation is monitored by thin layer chromatography. The reaction is quantitative after 4 hours. The reaction mixture is then concentrated under reduced pressure and the crude product, 4-N-p-toluenesulfonyl-2'-deoxycytidine obtained is concentrated by coevaporation with anhydrous pyridine (3×20 ml) and subsequently dissolved again in absolute pyridine (20 ml). 4,4'-dimethoxytrityl chloride (1.70 g, 5 mmol) is added. The tritylation reaction is observed by thin layer chromatography and is completed within 2 hours. The reaction mixture is partitioned between dichloromethane (50 ml) and 0.5M aqueous sodium bicarbonate solution (50 ml). The aqueous layer is additionally extracted with dichloromethane (2×50 ml) and the organic extracts are dried over anhydrous sodium sulfate and concentrated. Pure 5'-O-dimethoxytrityl-4-N-p-toluenesulfonyl-2'-deoxycytidine is obtained after chromatographic purification on a silica gel column with dichloromethane/methanol as the eluting agent. The product is dissolved in benzene (20 ml), frozen and lyophilized in an oil-pump vacuum. The pure product is isolated as a white solid substance. 2.520 g, 73.7% yield ab) Synthesis of the triethylammonium salt of 5'-O-dimethoxytrityl-4-N-p-toluenesulfonyl-2'-deoxycytidine-3'-O-monosuccinate 5'-O-dimethoxytrityl-4-N-p-toluenesulfonyl-2'-deoxycytidine (128 mg, 0.187 mmol), succinic acid anhydride (50 mg, 0.5 mmol) and 4-N,N-dimethylamino pyridine (DMAP, 3 mg, 0.02 mmol) are stirred with triethylamine (0.14 ml, 1 mmol) in anhydrous dichloromethane while excluding moisture. Analysis by thin-layer chromatography shows that the reaction is completed within 2 hours. The reaction mixture is partitioned between aqueous sodium bicarbonate (10 ml) and dichloromethane (10 ml). The aqueous layer is re-extracted with dichloromethane (2×10 ml), the combined extracts are dried over anhydrous sodium sulfate and concentrated. The remaining residue of the crude product is dissolved in 1,4-dioxan (3 ml), frozen and lyophilized under an oil-pump vacuum. The desired product forms as a white solid substance: 165 mg, 99% yield.

ac) Preparation of 5'-O-dimethoxytrityl-4-N-p-toluenesulfonyl-2'-deoxycytidine 3'-(2-cyanoethyl)-N,N-diisopropylphosphoramidite 5'-O-dimethoxytrityl-4-N-p-toluenesulfonyl-2'-deoxycytidine (1.368 g, 2 mmol) is stirred with a magnetic stirrer in anhydrous dichloromethane (10 ml) in the presence of diisopropylethylamine (2 ml, 11.5 mmol) and N,N-diisopropylamino-(2-cyanoethoxy)-chlorophosphine (0.535 ml, 2.40 mmol) is added to the described mixture while excluding moisture. The reaction is quantitative within ca. 15 min. as can be shown by TLC analysis. The reaction is stopped by addition of methanol (0.1 ml) and dichloromethane (30 ml) is added to the reaction mixture and it is extracted by shaking with aqueous sodium bicarbonate solution (20 ml). The aqueous phase is re-extracted with dichloromethane (2×10 ml) and the combined extracts are dried over anhydrous sodium sulfate. The crude product is purified chromatographically on a silica gel column using a mixture of n-hexane-acetone-triethylamine with a final composition of 10:85:5 (by volume) as the eluting agent. The desired pure product is isolated as a white powder by lyophilization from benzene (20 ml).

ad) Synthesis of 5'-O-dimethoxytrityl-4-N-(2,2'-(ethylenedioxy)-diethylamino)-2'-deoxycytidine Anhydrous 2,2'-(ethylenedioxy)-diethylamine (1.2 ml, 12 mmol) is added to a solution of 5'-O-dimethoxytrityl-4-N-p-toluenesulfonyl-2'-deoxycytidine (205 mg, 0.3 mmol) in 7.5 ml pyridine. The reaction vessel is sealed tight and placed overnight in an oven at 50° C. After cooling to room temperature, the reaction mixture is extracted with 15 ml water and 7.5 ml dichloromethane. The organic phase is dried over anhydrous sodium sulfate and concentrated by evaporation. The further purification is carried out by means of silica gel chromatography using a gradient of dichloromethane/methanol. Yield 170 mg (85% of theoretical yield) of a colourless foam.

ae) Synthesis of 5'-O-dimethoxytrityl-4-N-[8-(fluorescein-4-yl)thioureido-2,2'-(ethylenedioxy)diethylamino]-2'-deoxycytidine 5'-O-dimethoxytrityl-4-N-(2,2(-ethylenedioxy)diethylamino)-2'-deoxycytidine (66 mg, 0.01 mmol) is dissolved in 1 ml DMF. 0.1 ml sodium borate buffer (1M, pH 9.2) and fluorescein isothiocyanate (38 mg, 0.01 mmol) are added to this. The preparation is allowed to stand overnight in darkness at room temperature. The reaction mixture is extracted with sodium borate buffer (10 ml) and dichloromethane (10 ml). The emulsion is demulsified by centrifugation and the organic phase is separated. The extraction is repeated again twice. The combined organic phases are dried over sodium sulfate, the filtrate is concentrated by evaporation and the product is purified by means of reverse column chromatography (Merck, RP-2 silica gel) using a mixture of acetone and saturated aqueous sodium bicarbonate solution. 119 mg of the product is obtained as an orange coloured oil.

b) Deoxyadenosine carrier (FIG. 2)

ba) Synthesis of 6-N-p-toluenesulfonyl-2'-deoxyadenosine

Deoxyadenosine (1.15 g, 4.0 mmol) is co-evaporated three times with 10 ml anhydrous pyridine in each case and subsequently stirred for one hour at room temperature with trimethylsilyl chloride (4 ml, 32 mmol) in pyridine (120 ml). The mixture is then concentrated by evaporation to a volume of ca. 100 ml while excluding moisture. p-toluenesulfonyl chloride (1.83 g, 9.5 mmol) and dimethylaminopyridine (1.0 g, 9.3 mmol) are added and stirred for 50 hours at 60° C. under reflux while excluding moisture. A sample is taken in order to monitor the reaction, it is desilylated with concentrated ammonia (ca. 2 hours), rotary evaporated and taken up in dichloromethane. Examination by thin-layer chromatography (mobile solvent methylene chloride/methanol=9:1) shows that complete conversion cannot be obtained; the reaction is therefore stopped as soon as the decomposition products increase. The reaction volume is increased by addition of dichloromethane (100 ml), the mixture is subsequently extracted by shaking with a saturated sodium bicarbonate solution (250 ml) and the aqueous phase is re-extracted with dichloromethane (2×50 ml). The organic extracts are dried over sodium sulfate and the volume is subsequently concentrated by evaporation to ca. 100 ml in a water-jet vacuum. Concentrated aqueous ammonia solution (100 ml) is added and the course of the desilylation is monitored by thin-layer chromatography; the reaction is completed after 4 hours. Since a large number of decomposition products are formed, the crude product is purified over a gravity column with silica gel (Merck 7734) and methylene chloride/methanol 10:1 as the eluting agent.

bb) Synthesis of 5'-O-dimethoxytrityl-6-N-p-toluenesulfonyl-2'-deoxyadenosine

6-N-p-toluenesulfonyl-2'-deoxyadenosine (4.0 g, 9.8 mmol) is co-evaporated with absolute pyridine (3×15 ml), subsequently taken up in pyridine (50 ml) and 4,4'-dimethoxytrityl chloride (3.75 g, 11 mmol) is added under argon. Monitoring by thin-layer chromatography shows that the reaction is completed after 2 hours. Dichloromethane (50 ml) is added and the mixture is extracted by shaking with 0.5M sodium bicarbonate solution. The aqueous phase is re-extracted with dichloromethane (2×50 ml), the combined organic extracts are dried over sodium sulfate and rotary evaporated. The crude product obtained in this way is purified chromatographically on a silica gel column (Merck H 60) using methylene chloride/methanol as the eluting agent.

bc) Synthesis of the triethylammonium salt of 5'-O-DMTr-6-N-p-toluenesulfonyl-2'-deoxyadenosine-3'-O-monosuccinate 5'-O-DMTr-6-N-p-toluenesulfonyl-2'-deoxyadenosine (200 mg, 0.28 mmol), succinic acid anhydride (70 mg, 0.7 mmol), 4-N,N-dimethylaminopyridine (DMAP, 4.5 mg, 0.03 mmol) and absolute triethylamine (0.2 ml, 1.4 mmol) are dissolved in absolute methylene chloride and stirred for 2 hours at room temperature. The reaction mixture is then partitioned between aqueous sodium bicarbonate (10 ml) and dichloromethane (10 ml), the aqueous phase is re-extracted with dichloromethane (2×10 ml), the combined organic phases are dried over sodium sulfate and rotary evaporated. The product obtained in this way is then processed further without purification.

bd) Synthesis of 5'-O-dimethoxytrityl-8-(2,2'-(ethylenedioxy)-diethylamino)-2'-deoxyadenosine Anhydrous 2,2-(ethylenedioxy)-diethylamine (0.5 ml) is added to a solution of 5'-O-dimethoxytrityl-8-bromo-2'-deoxyadenosine (100 mg, 0.15 mmol) in 0.5 ml pyridine. The reaction vessel is tightly sealed and stored overnight in an oven at 70° C. It is further processed and purified analogous to the procedure for 5'-O-dimethoxytrityl-4-N-2,2'-(ethylenedioxy)-diethylamino)-2'-deoxycytidine as in example ad).

be) Synthesis of 5'-O-dimethoxytrityl-8-8-(fluorescein-4-yl)thioureido-2,2'-(ethylenedioxy)-diethylamino)-2'-deoxyadenosine 5'-O-dimethoxytrityl-8-N-(2,2'-(ethylenedioxy)-diethylamino)-2'-deoxyadenosine (82 mg, 0.12 mmol) is dissolved in 1 ml DMF. 0.1 ml sodium borate buffer (1M, pH 9.2) and fluorescein isothiocyanate (47 mg, 0.12 mmol) is added to this. The preparation is allowed to stand overnight in darkness at room temperature. The reaction mixture is extracted with sodium borate buffer (10 ml) and dichloromethane (10 ml). The emulsion is demulsified by centrifugation and the organic phase is separated. The extraction is repeated for a further two times. The combined organic phases are dried over sodium sulfate, the filtrate is concentrated by evaporation and the product is purified by means of reverse column chromatography (Merck, RP-2 silica gel) using a mixture of acetone and saturated aqueous sodium bicarbonate solution. 97 mg of the product is obtained as an orange coloured oil.

c) Deoxyguanosine carrier

Figure 3:
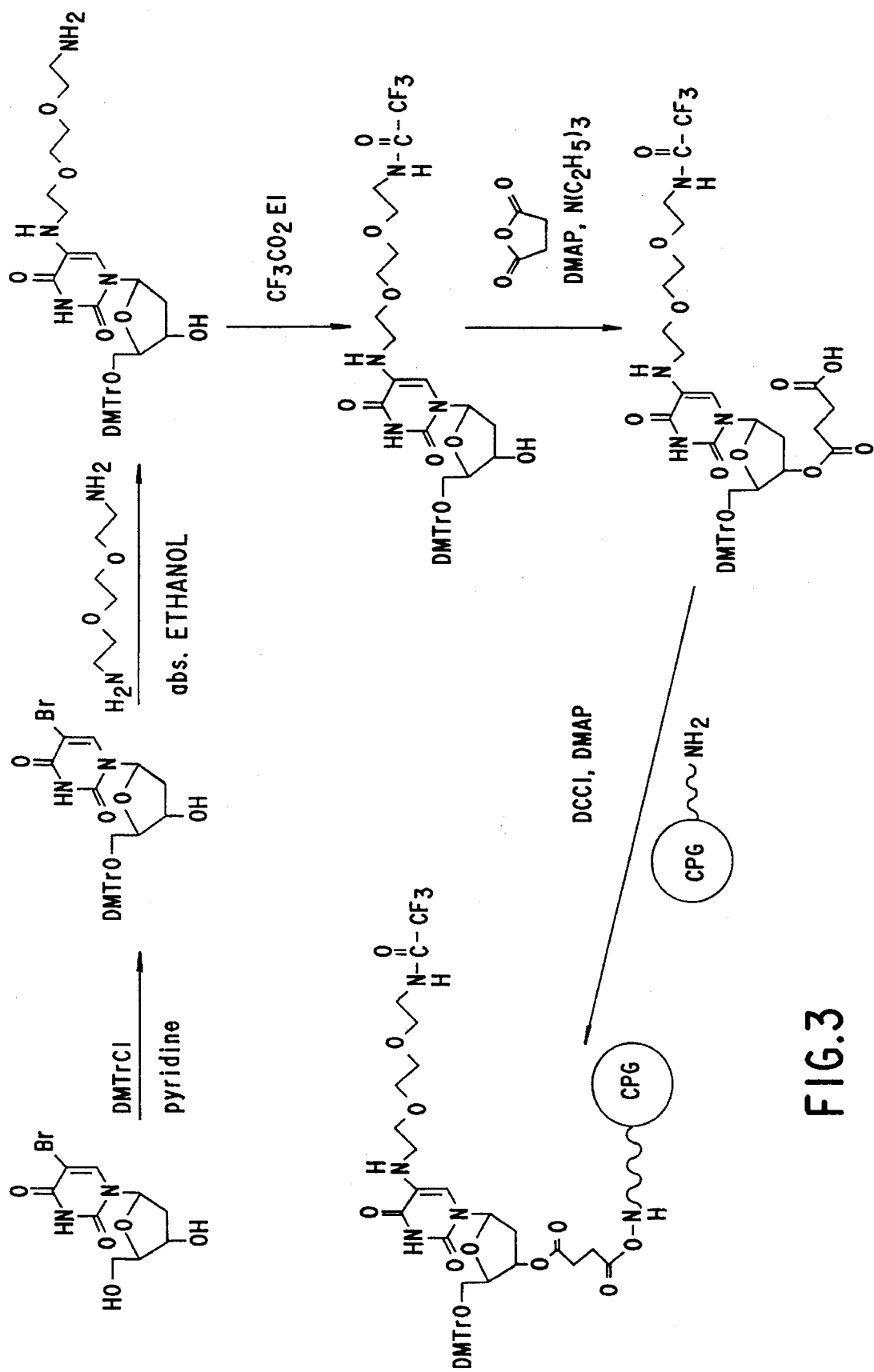
FIG. 3 shows the synthesis of a deoxyuridine carrier which (already) contains the spacer starting with a halogenated nucleoside derivative.
Figure 4:
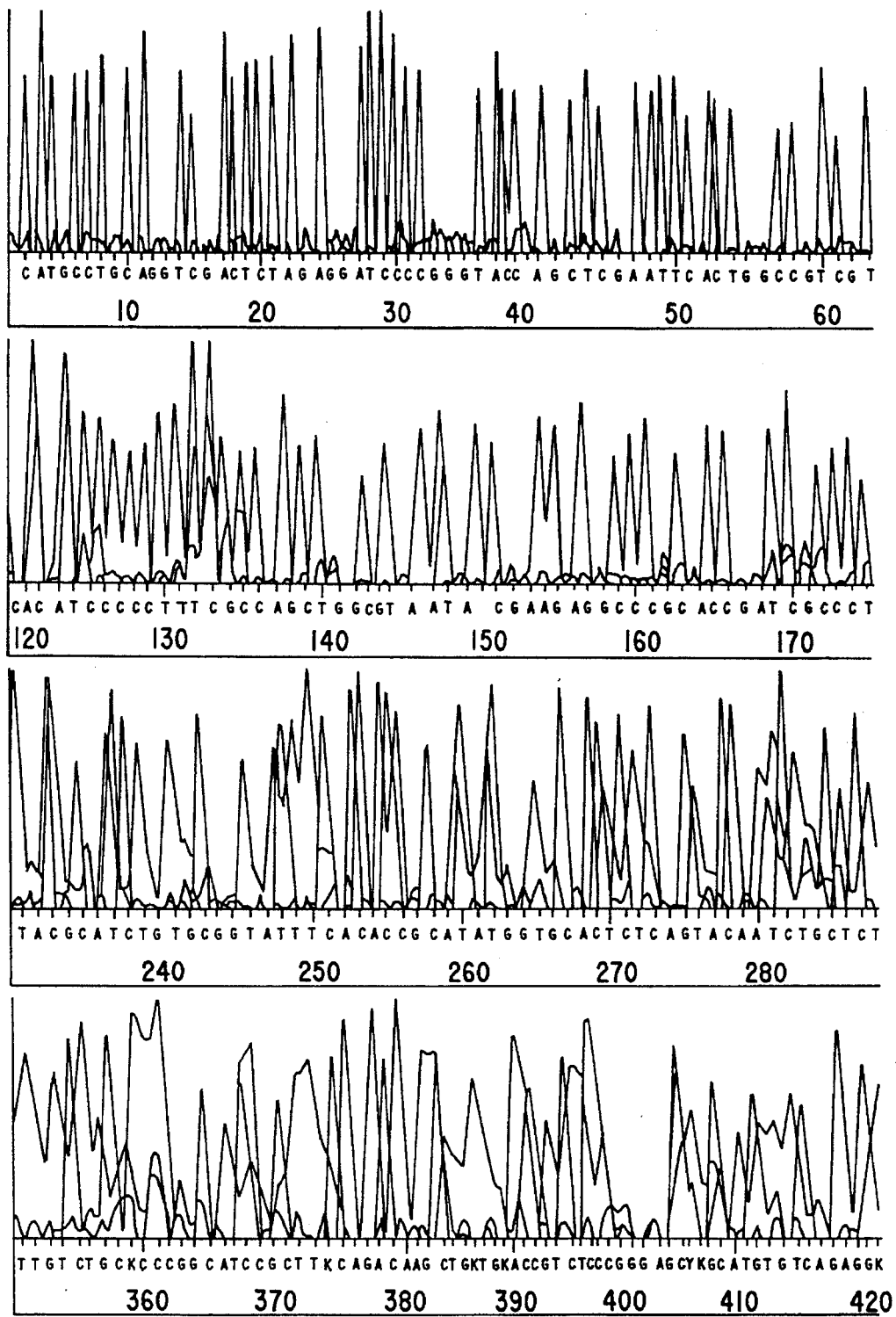
FIGS. 4 and 5 concern the sequencing of pUC DNA with primer RP.
Figure 5:
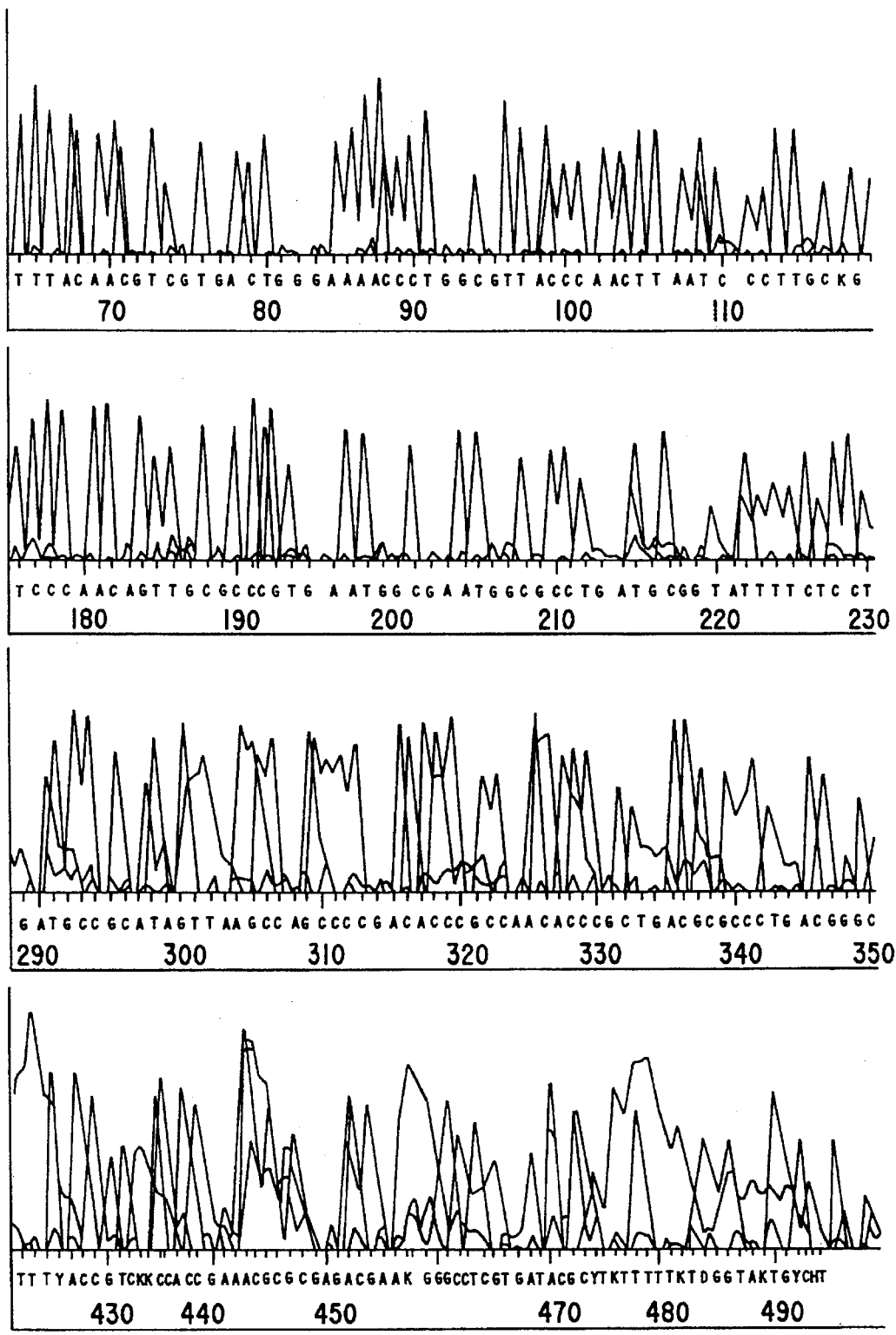
Figure 6:
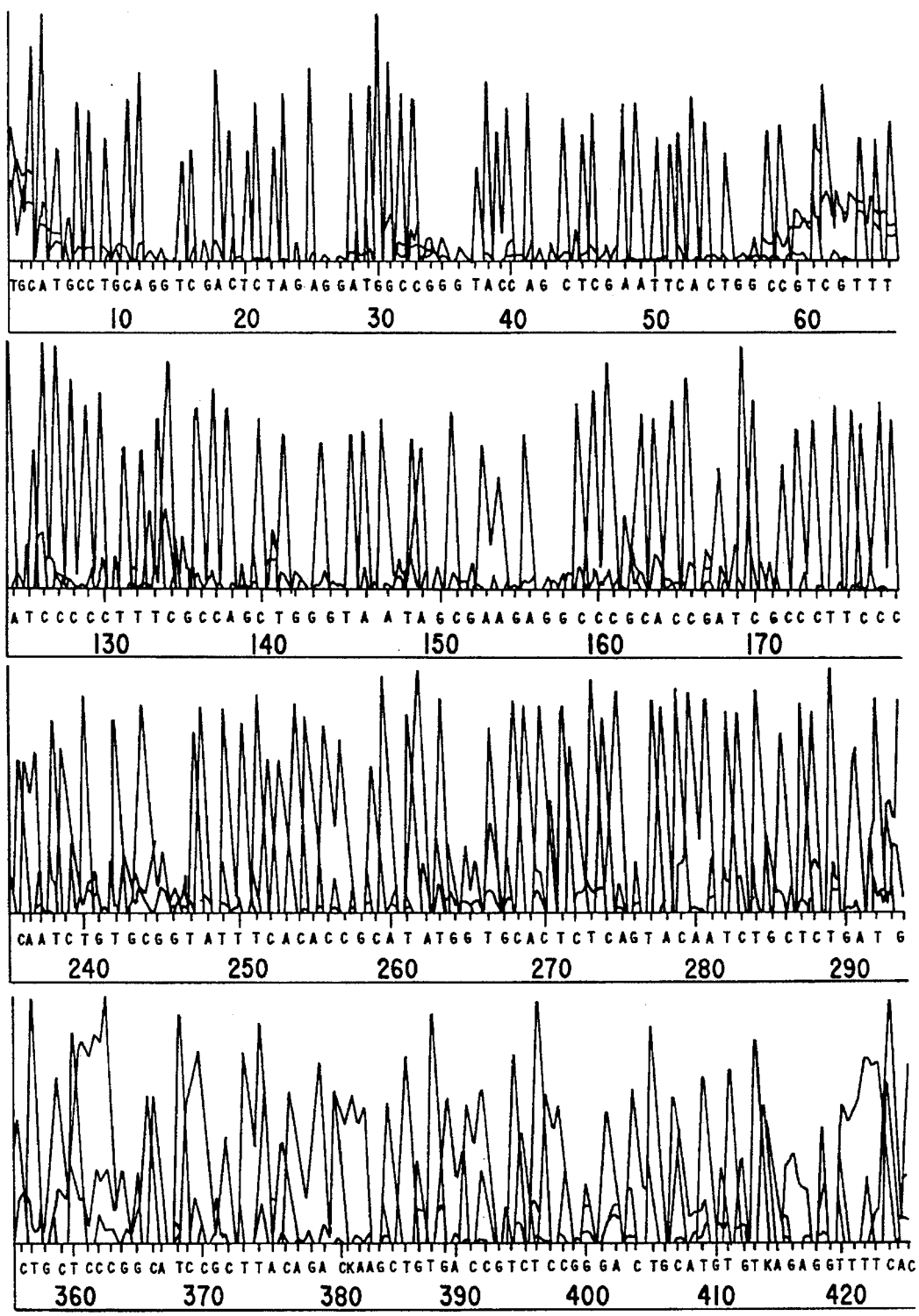
FIGS. 6 and 7 concern the sequencing of pUC DNA with primer A.
Figure 7:
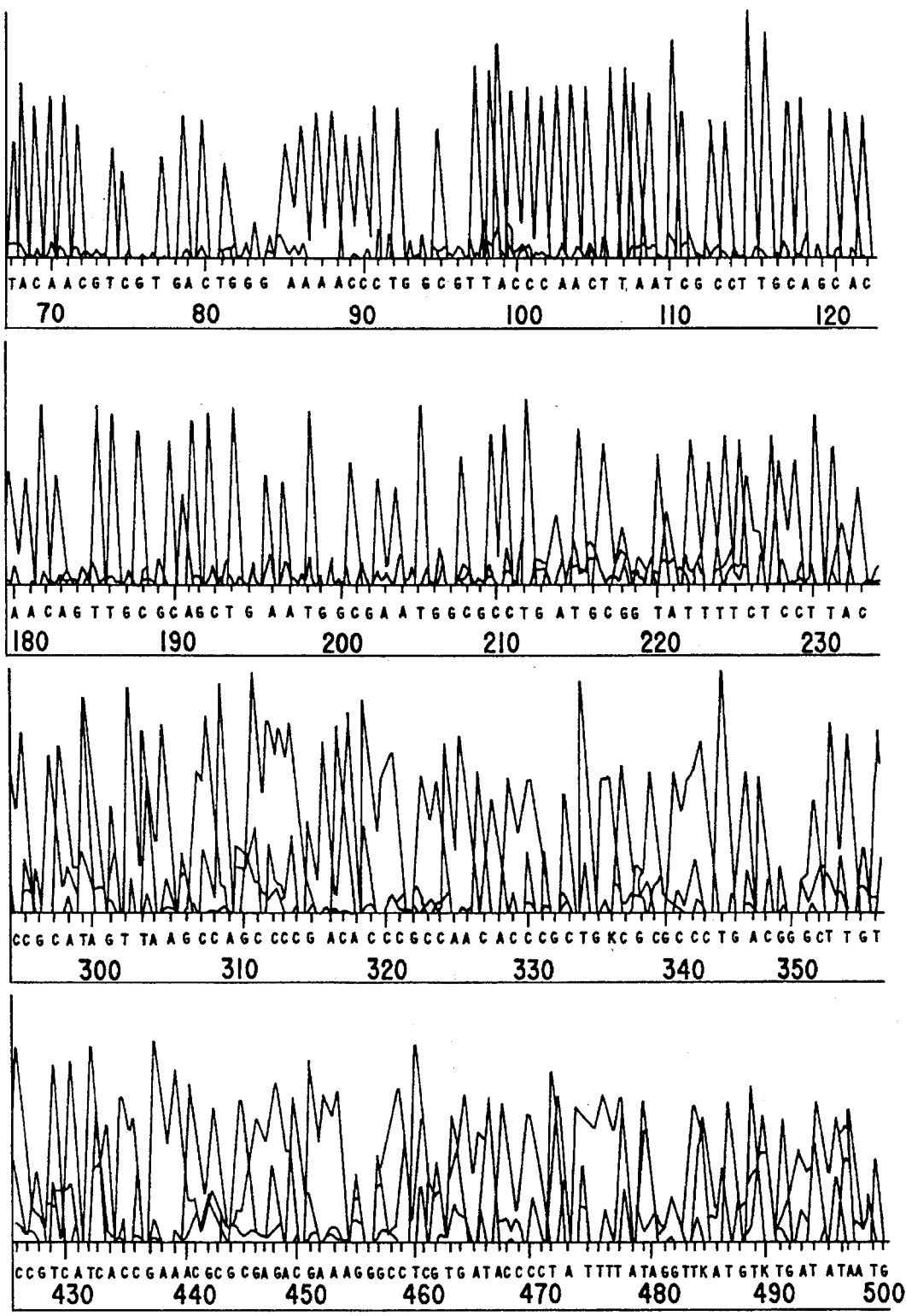
Figure 8:
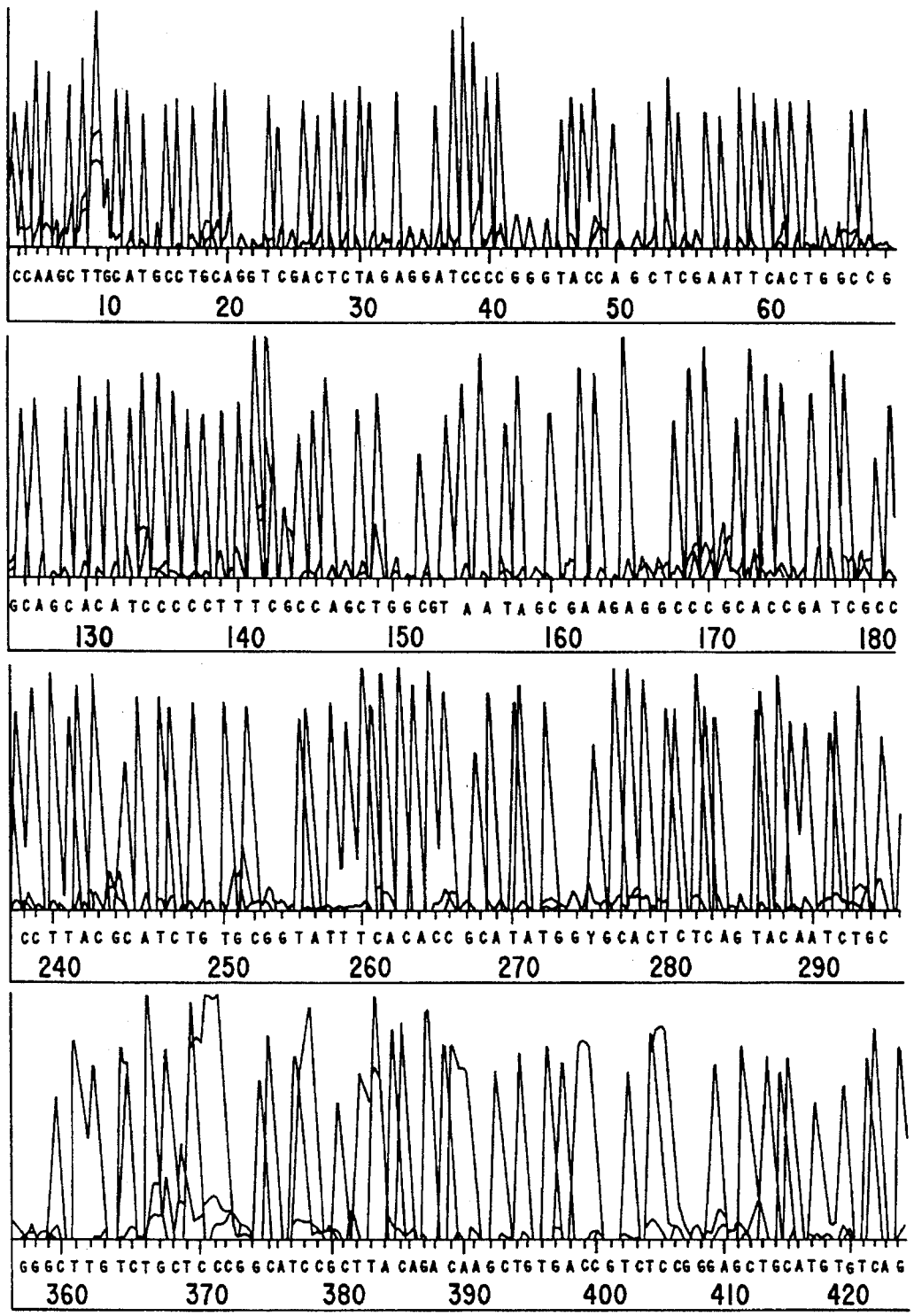
FIGS. 8 and 9 concern the sequencing of pUC DNA with primer B.
Figure 9:
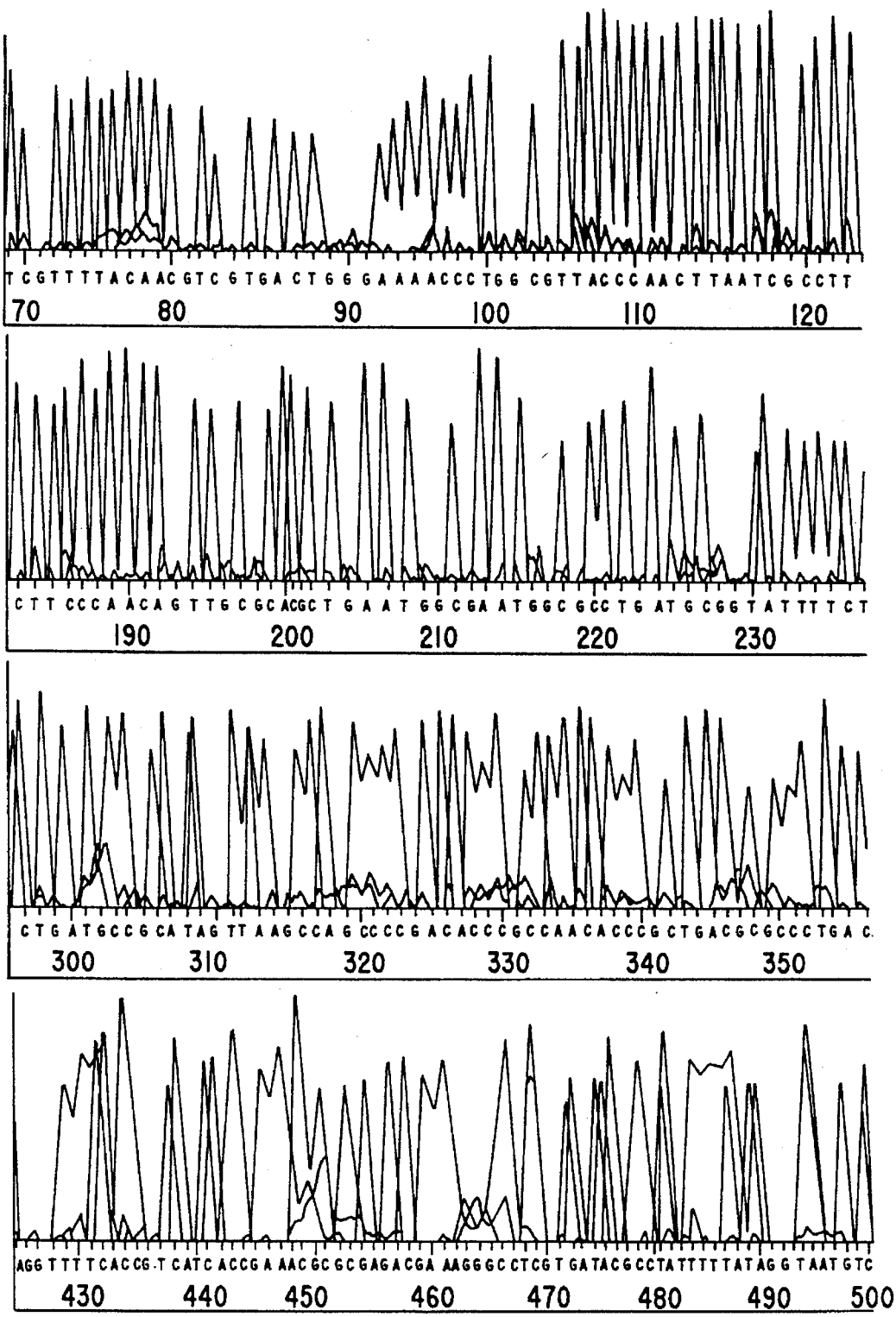
Figure 10:
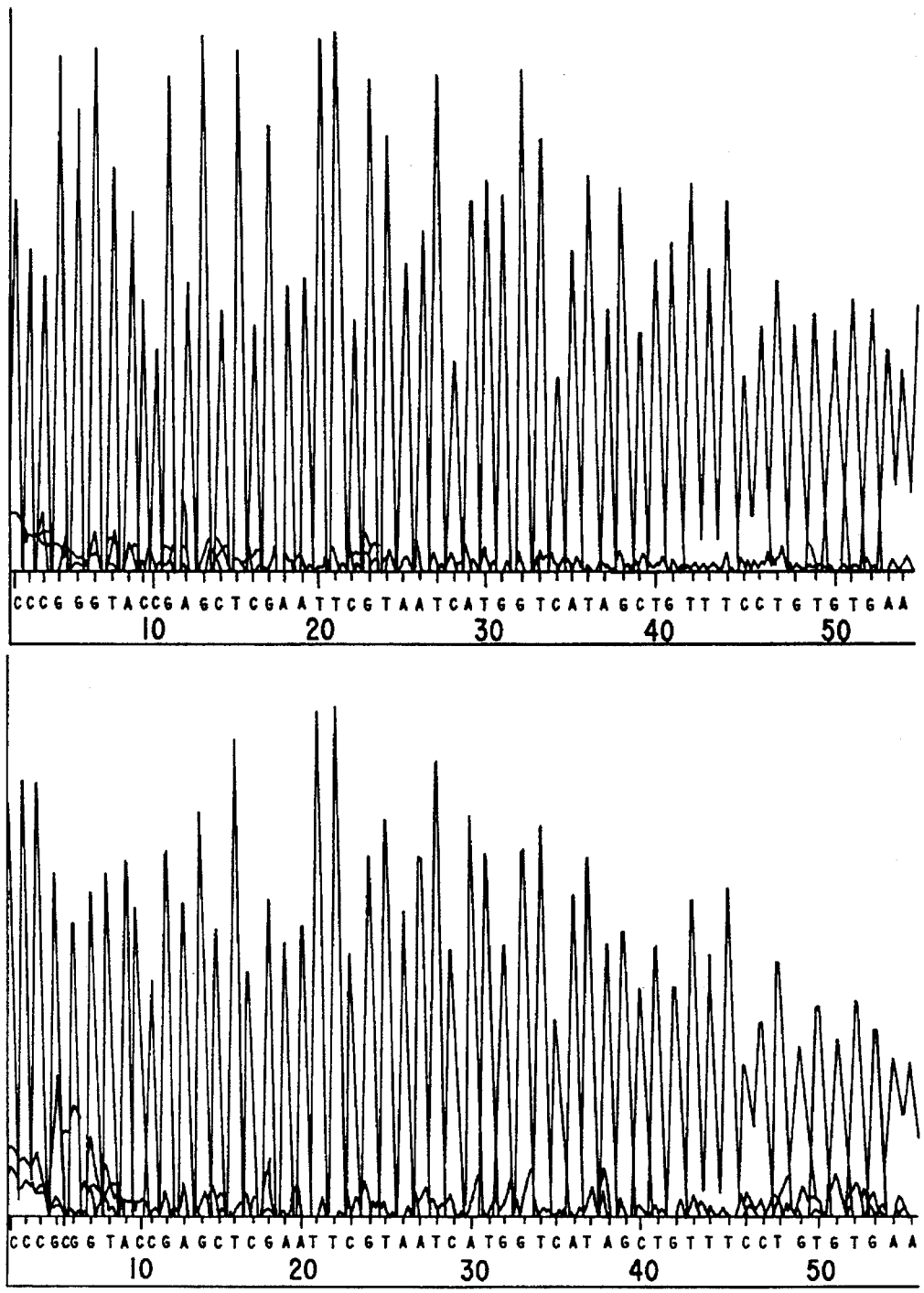
FIGS. 10 and 11 concern the sequencing of M13 DNA with primer D.
Figure 11:
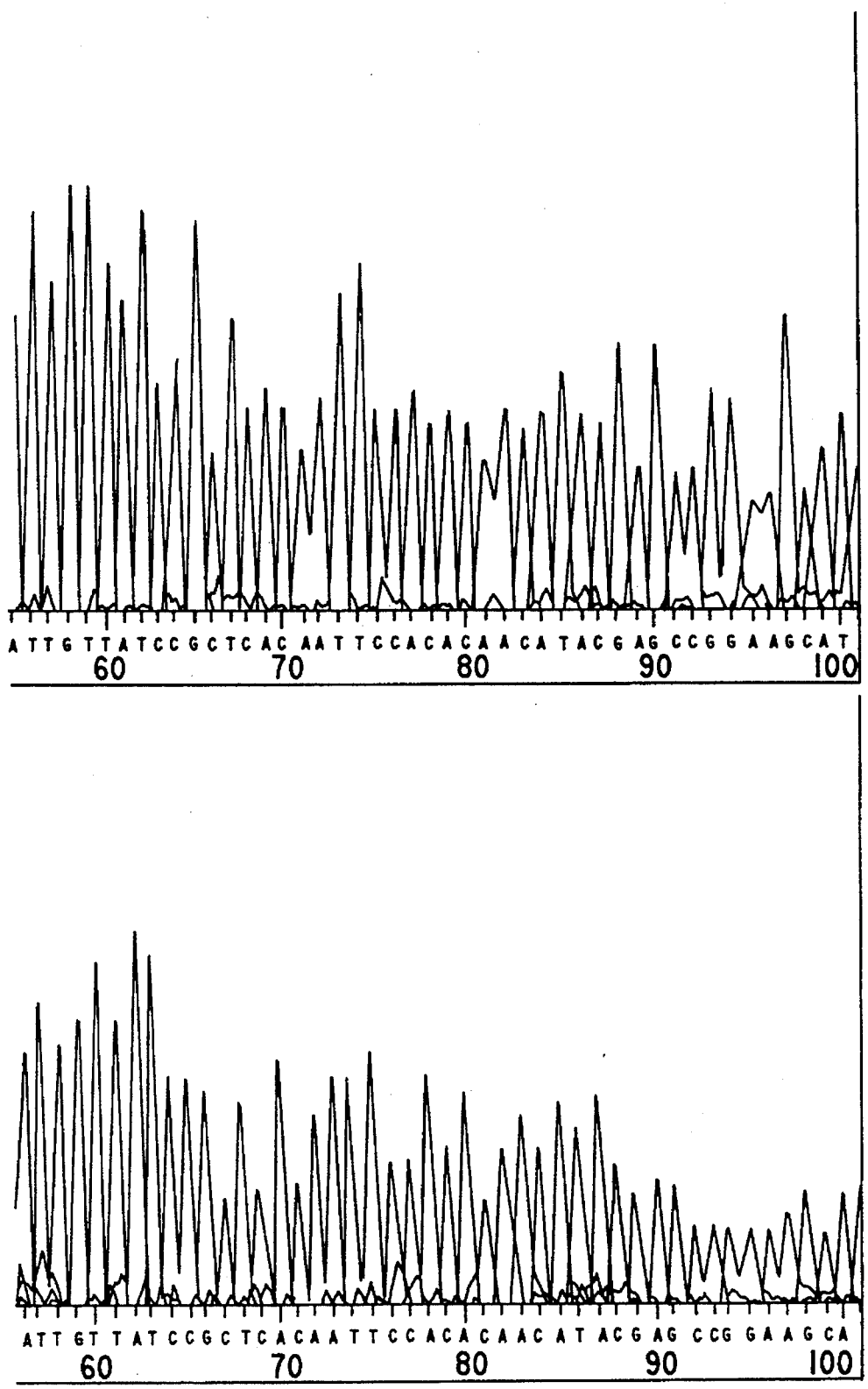
Figure 12:
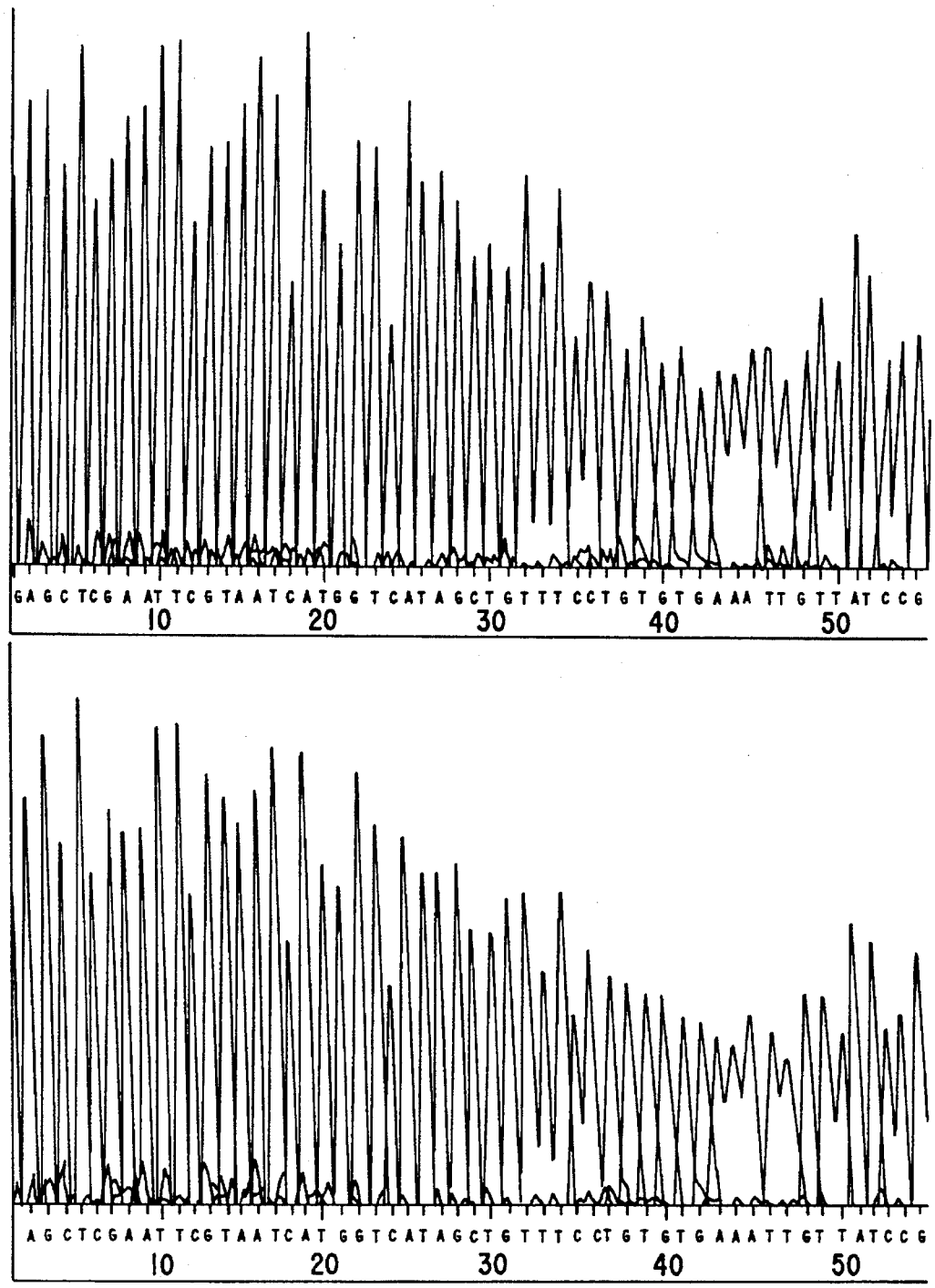
FIGS. 12 and 13 concern the sequencing of M13 DNA with primer E.
Figure 13:
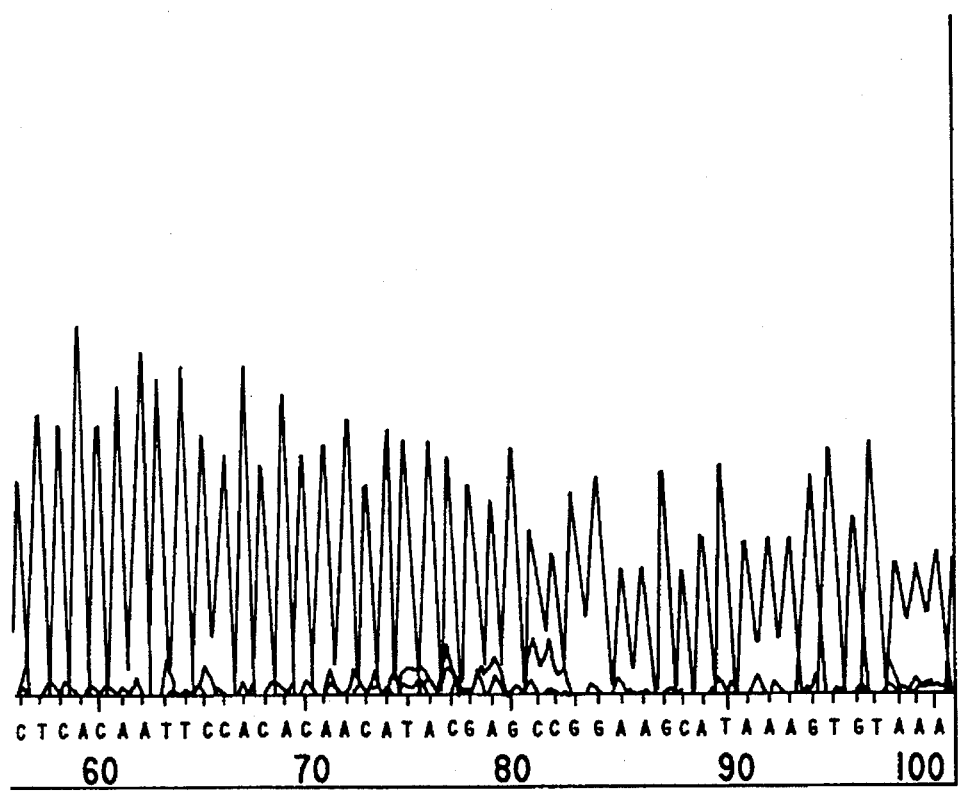
Figure 13:
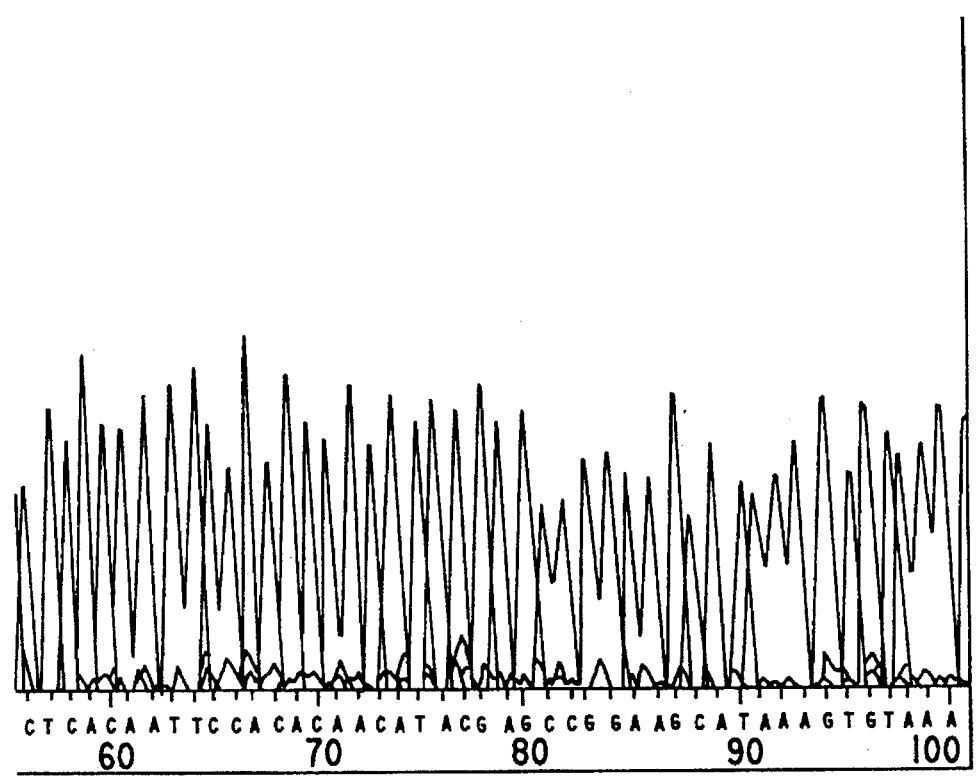

The synthesis of 5'-O-DMTr-2-N-p-toluenesulfonyl-2'-deoxyguanosine is carried out analogous to bb) (FIG. 2).

d) Deoxyuridine carrier (FIG. 3)

da) Synthesis of 5'-O-dimethoxytrityl-5-bromo-2'-deoxyuridine 5-bromo-2'-deoxyuridine (4.0 g, 13 mmol) is co-evaporated with absolute pyridine (3×15 ml), subsequently taken up in pyridine (50 ml) and 4,4'-dimethoxytrityl chloride (4.88 g, 14.3 mmol) is added under argon. Monitoring by thin-layer chromatography shows that the reaction is completed after 2 hours. Dichloromethane (50 ml) is added and the mixture is extracted by shaking with 0.5M sodium bicarbonate solution. The aqueous phase is re-extracted with dichloromethane (2×50 ml), the combined organic extracts are dried over sodium sulfate and rotary evaporated. The crude product obtained in this way is purified chromatographically on a silica gel column using methylene chloride/methanol as the eluting agent.

db) Synthesis of 5'-O-dimethoxytrityl-5(2,2'-(ethylene dioxy)-diethylamino)-2'-deoxyuridine 5'-O-dimethoxytrityl-5-bromo-2'-deoxyuridine (0.7 g, 1.2 mmol) is dissolved in absolute ethanol (10 ml) while excluding moisture. Dry 2,2'-(ethylenedioxy)-diethylamine (0.7 ml, 4.8 mmol) is added and the mixture is heated for 24 hours under reflux. Subsequently the solution is concentrated until dryness by evaporation in a vacuum. The oily residue is taken up in dichloromethane (30 ml) and extracted with saturated potassium chloride solution (2×30 ml) in order to remove most of the excess diamine. The organic phase is dried over sodium sulfate and rotary evaporated. The residue is digested with a little water (2–3 ml) in order to further remove the diamine. The water is drawn off and discarded. The product is dried in a desiccator over phosphorus pentoxide in an oil-pump vacuum until it takes on a powdery consistency.

EXAMPLE 2

General Instructions for the Production of Labelling Phases for Oligonucleotide Synthesis Using Succinic Acid Esters of the Protected Labelled Nucleosides The triethylammonium salt of the nucleoside succinate protected in a suitable manner (0.185 mmol, e.g. example 1 bc), a carrier material (1.0 g), N,N-dicyclohexylcarbodimine (200 mg, 1 mmol), 4-N,N-dimethylaminopyridine (DMAP, 6 mg, 0.05 mmol), triethylamine (0.07 ml, 0.5 mmol) are shaken overnight at room temperature in anhydrous dichloromethane (3 ml) in the absence of air. The carrier is then filtered off, washed with dichloromethane (50 ml) and transferred into a flask with acetic anhydride (0.35 ml), triethylamine (1 ml), DMPA (12 mg) in dichloromethane (2 ml) for the masking reaction and allowed to react for 2 hours. The carrier is filtered off and washed successively with dichloromethane, methanol, dichloromethane and diethyl ether (25 ml in each case) and dried in a desiccator in an oil.pump vacuum until the weight remains constant.

The LCAA-CPG 500 A carrier with 5'-O-dimethoxytrityl-4-N-p-toluenesulfonyl-2'-deoxycytidine (or -adenosine) is produced in accordance with the instructions described above with a loading of 18 µmol/g (or 26 µmol/g with the adenosine derivative).

Derivatization of "long chain aminoalkyl" controlled pore glass carriers (LCAA-CPG 500) with 4-N-p-toluenesulfonyl-2'-deoxycytidine or with 6-N-p-toluenesulfonyl-2'-deoxyadenosine The triethylammonium salt of 5'-O-dimethoxytrityl-p-toluenesulfonyl-2'-deoxynucleoside-3'-O-monosuccinate (0.186 mmol), LCAA-CPG 500 A (Pierce Company, 1000 g), N,N'-dicyclohexylcarbodiimide (200 mg, 1 mmol), 4-N,N-dimethylaminopyridine (DMAP, 6 mg, 0.05 mmol) and triethylamine (0.07 ml, 0.5 mmol) are carefully mechanically shaken overnight at room temperature while excluding moisture. The carrier is filtered off, washed with dichloromethane (50 ml) and transferred into a reaction flask for masking unreacted hydroxyl groups, shaken for 2 hours with acetic anhydride (0.35 ml), triethylamine (1 ml), DMAP (12 mg) in dry dichloromethane (2 ml). The carrier is filtered off, washed successively with dichloromethane, methanol, dichloromethane and diethyl ether (25 ml in each case) and dried in a desiccator in an oil-pump vacuum until the weight remains constant. The loading of the carrier is estimated by spectophotometric measurement of the dimethoxytrityl cation which is carried out using a small sample of the carrier after treatment with acid according to the method described in the literature and is 18 µmol/g for the cytidine derivative and 26 µmol/g for the adenosine derivative.

The reaction is carried out analogously with other carrier materials loaded with amino groups (e.g. CPG 1400).

Derivatization of LCAA-CPG 500 with 5'-O-dimethoxytrityl-8-(8-fluorescein-4-yl)thioureido-2,2'-(ethylenedioxy)-diethylamino)-2'-deoxyadenosine or with 5'-O-dimethoxytrityl-4-N-(8-fluorescein-4-yl)thioureido-2,2'-(ethylenedioxy)-diethylamino-2'-deoxycytidine 5'-O-dimethoxytrityl-8-(8-fluorescein-4-yl)thioureido-2,2-(ethylenedioxy)-diethylamino)-2'-deoxyadenosine (55 mg, 0.05 mmol) is dissolved in dichloromethane/pyridine (1:1, 3.5 ml) and triethylamine (0.3 ml), 4-N,N-dimethylaminopyridine (DMAP, 12 mg) and succinic acid anhydride (200 mg) are added. It is allowed to react overnight in darkness at room temperature. Subsequently the reaction mixture is concentrated by evaporation and extracted with dichloromethane/aqueous sodium bicarbonate solution. After drying over sodium sulfate, the organic phase is concentrated by evaporation and co-evaporated with pyridine. LCAA-CPG 500 Å (300 mg, Pierce Company), DMAP (6 mg), triethylamine (0.07 ml), dicyclohexylcarbodiimide (DCCI, 200 mg) and dichloromethane (1.5 ml) are added to the crude product obtained in this way. The reaction mixture is shaken overnight at room temperature, the carrier is filtered off and washed with dichloromethane, methanol and diethyl ether. Afterwards the derivatized carrier is transferred into a round-bottom flask and acetic anhydride (0.5 ml), pyridine (1 ml), DMAP (12 mg) and dichloromethane (5 ml) are added. The carrier is filtered off after 3 hours, washed and dried in a desiccator in an oil-pump vacuum. The loading of the carrier is 19.6 µmol/g for the adenosine derivative and 9.5 µmol/g for the cytidine derivative.

Primer D and primer E described in example 5 were synthesized with these carriers.

EXAMPLE 3

General Working Instructions for the Synthesis of Labelled Oligonucleotides Using Labelling Phases a) Synthesis of oligonucleotides with p-toluenesulfonyl groups and their reaction with 2,2'-(ethylenedioxy)-diethylamine Oligonucleotides are synthesized using the Gene Assembler Plus from the Pharmacia LKB Company (Sweden) according to the protocol of the manufacturer in which suitable carrier materials (0.2 µmol) and phosphoramidites are used. The oligonucleotides are cleaved off within one hour from the carrier by treatment with concentrated aqueous ammonia at room temperature in an Eppendorf reaction vessel. The pooled solution is concentrated to dryness in a Speed-vac evaporator. Anhydrous 2,2'-(ethylenedioxy)-diethylamine (100 µl) is added to the partially deprotected oligonucleotides, the reaction vessel is closed and the oligonucleotide is dissolved at room temperature in an ultrasonic bath (5 to 10 min). The reaction solution is placed overnight in an incubator at 80° C. The product which is completely deprotected with the exception of the p-toluenesulfonyl groups is precipitated from the amine solution. The reaction vessel is centrifuged and the solution is carefully removed. Anhydrous ethanol (100 µl) is added, the precipitate is washed with the aid of an ultrasonic bath (5 to 10 min) and centrifuged. The supernatant is discarded and the washing procedure is repeated once. The precipitate of the crude product is dried in a Speed vac evaporator and used in further experiments.

b) Reaction of aminoalkyl-oligonucleotides with fluorescein isothiocyanate

The process for introducing fluorescein residues into oligonucleotides is essentially the same as stated in the protocol of the Pharmacia LKB Company (Pharmacia-LKB Autoprimer™ Synthesis Kit (27-9290-01). The precipitate of the unpurified oligonucleotide is dissolved in 0.15M sodium borate buffer pH 9.2 (100 µl) and a freshly prepared solution of fluorescein isothiocyanate isomer I (1 mg) in anhydrous dimethylsulfoxide (30 µl) is added. The reaction is carried out in darkness at room temperature for 4 to 20 hours with essentially the same results. The reaction mixture is applied to a NAP-10 column (Pharmacia-LKB) and washed with redistilled water (pH 8 to 9.5, adjusted with ammonia). The fractions containing the oligonucleotides (1.3 ml) are pooled and the desired, labelled oligonucleotide is isolated by means of polyacrylamide gel electrophoresis (20%, 7M urea) or by HPLC and characterized with the aid of UV-Vis spectrometry. Cleavage with snake venom phosphodiesterase/alkaline bovine phosphatase is carried out according to (Anal. Biochem. 165, 442–447 (1987).

c) Synthesis of oligonucleotides using carriers with fluoresceinated deoxynucleotides The oligonucleotides are synthesized with suitable phosphoramidites using the Gene Assembler Plus from the Pharmacia-LKB Company (Sweden) in accordance with the manufacturer's protocol. The LCAA-CPG 500 A carrier (10 mg, 0.2 µmol) derivatized with fluorescein-deoxynucleotides is used as the carrier material. The cleavage of the synthesized oligonucleotide and the further processing are carried out analogous to the standard protocol of Pharmacia. Further purification is carried out by polyacrylamide gel electrophoresis (20%, 7M urea) or by means of reverse phase HPLC.

EXAMPLE 4

Use of 3'-Terminally Labelled Oligonucleotides in Template-Dependent Chain Extension Catalysed by DNA Polymerase Sequencing investigations were carried out using the following modified oligonucleotides as an example:

| Primer A: | 5'-CAGGAAACAGCTATAGX | SEQ. ID. NO: 1 |
|---|---|---|
| Primer B: | 3'-XAGGAAACAGCTATGAC | SEQ. ID. NO: 2 |

(both primers were prepared according to 3a, b))
X=cytidine labelled with fluorescein An analogous primer reacted in the usual way with an amino linker at the 5'-position and labelled with fluorescein was used as the reference substance (primer RP) (instructions of Pharmacia Company). pUC 19 as well as octopus DNA (D3) were used as the DNA to be investigated.

The sequencing is carried out for all primers according to the Sanger dideoxy method following the working instructions of the Pharmacia Company. The sequencing results on pUC 19 DNA are shown in FIGS. 4 through 9.

It was sequenced analogously using the following primer:

Primer C: 5'-TTTCACACAGGAAACAGCTATGY  SEQ. ID. NO: 3

Y=adenosine labelled with fluorescein.

EXAMPLE 5

Use of 3'-Terminally Labelled Oligonucleotides in the M13 Standard Sequencing System Two variants of the universal M13 sequencing primer were used for the sequencing investigations:

| Primer D: | 5'-TTGTAAAACGACGGCCY (prepared according to 3c) | SEQ. ID. NO: 4 |
|---|---|---|
| Primer E: | 5'-AAAACGACGGCCAGTGX | SEQ. ID. NO: 5 |

(both primers were prepared according to 3c))
Y=adenosine labelled with fluorescein
X=cytidine labelled with fluorescein.

M13mp18 (Pharmacia Co.) was used as the DNA to be investigated.

The sequencing for both primers was carried out according to the Sanger dideoxy method following the working instructions of the Pharmacia Co. (T7 sequencing kit). The sequencing results are shown in FIGS. 10 through 13.

We claim:

1. A polymeric carrier covalently bound to a nucleoside or nucleotide or a precursor thereof via an anchor group and a spacer group, wherein said spacer group contains an ethylenedioxy group, wherein said nucleoside or nucleotide or precursor thereof is covalently linked or linked via a spacer to a labeling group, and wherein said labeling group is covalently linked to the nucleobase of said nucleoside or nucleotide or precursor thereof.

2. The carrier according to claim 1, wherein the nucleoside, nucleotide or precursor thereof is attached to the anchor group via its 3'-hydroxyl group.

3. The carrier according to claim 1, wherein said polymeric carrier is selected from the group consisting of polystyrene derivatives, silica gel, controlled pore glass and soluble derivatives of polyethylene glycol.

4. The carrier according to claim 1, wherein said nucleoside is a mononucleoside.

5. A method for synthesizing labelled oligonucleotides comprising the steps of:
    a) hybridizing an oligonucleotide chain with a target nucleic acid, and
    b) extending said oligonucleotide chain using a template dependent DNA or RNA polymerase, wherein the 3'end of said oligonucleotide chain contains at least one moiety selected from the group consisting of deoxynucleosides or ribonucleosides, deoxynucleotides or ribonucleotides and precursors thereof covalently linked or linked via a spacer to a non-radioactive labelling group, wherein said labeling group is linked to the nucleobase of said nucleoside or nucleotide or precursor thereof.

6. A method for enzymatic nucleic acid sequencing, comprising the steps of:
    a) hybridizing an oligonucleotide chain with a target nucleic acid,
    b) enzymatically elongating said oligonucleotide chain in the presense of a specific chain terminator, and
    c) determining the nucleic acid sequence of the target nucleic acid based on the elongated oligonucleotide chain,
    wherein the 3'end of said oligonucleotide chain has a defined number and type of deoxynucleosides or ribonucleosides, deoxynucleotides or ribonucleotides or precursors thereof covalently linked or linked via a spacer to a non-radioactive labelling group wherein said labeling group is linked to the nucleobase of said nucleoside or nucleotide or precursor thereof.

7. A method for polymerase chain reaction comprising the steps of:
    a) hybridizing said oligonucleotide chain with a target nucleic acid in a sample solution,
    b) enzymatically elongating said oligonucleotide chain to form an extension product,
    c) separating the extension product from the target nucleic acid,
    d) adding oligonucleotide primers produced to said sample solution, wherein both the extension product and the target nucleic acid act as templates for the production of further extension products,
    wherein the 3'end of said oligonucleotide chain contains at least one moiety selected from the group consisting of deoxynucleosides or ribonucleosides, deoxynucleotides or ribonucleotides and precursors thereof covalently linked or linked via a spacer to a non-radioactive labelling group wherein said labeling group is linked to the nucleobase of said nucleoside or nucleotide or precursor thereof.

8. Process for the production of labelled nucleic acids, comprising the steps of:
    a) hybridizing a primer to a template nucleic acid, and
    b) enzymatically extending said primer,
    wherein said primer contains a nucleoside with a non-radioactive labelling group at its 3' end linked to the nucleobase of said nucleoside.

9. Process for the production of terminal-nucleotide labelled oligonucleotides by chemical synthesis on a polymeric carrier, comprising the steps of elongating a nucleoside or nucleotide or a precursor thereof which is covalently bound to a polymeric carrier via an anchor group and a spacer group which contains an ethylenedioxy group, by linkage with further mononucleoside units,
    wherein said nucleoside or nucleotide or a precursor thereof is covalently linked or linked via a spacer to a labelling group, and wherein said labeling group is linked to the nucleobase of said nucleoside or nucleotide or precursor thereof.

10. Labeled oligonucleotides comprising a 3' end with a spacer group which contains an ethylenedioxy group and at least one moiety selected from the group consisting of deoxynucleosides or ribonucleosides, deoxynucleotides or ribonucleotides and precursors thereof covalently linked or linked via a spacer to a labeling group, and wherein said labeling group is linked to the nucleobase of said nucleoside or nucleotide or precursor thereof.

11. A method for synthesizing 3' terminal labelled oligonucleotides comprising the steps of:
    a) reacting an anchor group attached to a polymeric carrier with a nucleoside, wherein said nucleoside is covalently linked or linked via a spacer to a labeling groups, and wherein said labeling group is linked to the nucleobase of said nucleoside or nucleotide or precursor thereof,
    b) synthesizing an oligonucleotide chain incorporating said nucleoside,
    c) cleaving said oligonucleotide chain from said polymeric, wherein said cleavage, said labeling group is at the 3'end of the oligonucleotide chain.

12. A method for template-dependent, DNA or RNA polymerase-catalyzed chain extensions, comprising the steps of:
    a) reacting an anchor group with a nucleoside, wherein said anchor group is attached to a polymeric carrier, and wherein said nucleoside is covalently linked or linked via a spacer to a labeling group, b) synthesizing an oligonucleotide chain incorporating said nucleoside, c) cleaving said oligonucleotide chain from said polymeric carrier, wherein after cleavage, said labeling group is at the 3'end of the oligonucleotide chain, d) hybridizing said oligonucleotide chain with a target nucleic acid, and e) extending said oligonucleotide chain using a template dependent DNA or RNA polymerase, wherein the 3'end of said oligonucleotide chain has at least one moiety selected from the group consisting of deoxynucleosides or ribonucleosides, deoxynucleotides or ribonucleotides or precursors thereof covalently linked or linked via a spacer to a non-radioactive labelling group wherein said labeling group is linked to the nucleobase of said nucleoside or nucleotide or precursor thereof.

13. A method for enzymatic nucleic acid sequencing, comprising the steps of:

a) reacting an anchor group with a nucleoside, wherein said anchor group is attached to a polymeric carrier, and wherein said nucleoside is covalently linked or linked via a spacer to a labeling group, b) synthesizing an oligonucleotide chain incorporating said nucleoside, c) cleaving said oligonucleotide chain from said polymeric carrier, wherein after cleavage, said labeling group is at the 3'end of the oligonucleotide chain, d) hybridizing said oligonucleotide chain with a target nucleic acid, and e) enzymatically elongating said oligonucleotide chain in the presence of a specific chain terminator, and f) determining the nucleic acid sequence of the target nucleic acid based on the elongated oligonucleotide chain, wherein the 3'end of said oligonucleotide chain has at least one moiety selected from the group consisting of deoxynucleosides or ribonucleosides, deoxynucleotides or ribonucleotides and precursors thereof covalently linked or linked via a spacer to a non-radioactive labelling group wherein said labeling group is linked to the nucleobase of said nucleoside or nucleotide or precursor thereof.

14. A method for polymerase chain reaction comprising the steps of:

a) reacting an anchor group with a nucleoside, wherein said anchor group is attached to a polymeric carrier, and wherein said nucleoside is covalently linked or linked via a spacer to a labeling group, b) synthesizing an oligonucleotide chain incorporating said nucleoside, for use as a primer, c) cleaving said oligonucleotide chain from said polymeric carrier, wherein after cleavage, said labeling group is at the 3'end of the oligonucleotide chain, d) hybridizing said oligonucleotide chain with a target nucleic acid in a sample solution, e) enzymatically elongating said oligonucleotide chain to form an extension product, f) separating the extension product from the target nucleic acid, g) adding oligonucleotide primers produced according to steps a)–c) to said sample solution, wherein both the extension product and the target nucleic acid act as templates for the production of further extension products, wherein the 3'end of said oligonucleotide chain has at least one moiety selected from the group consisting of deoxynucleosides or ribonucleosides, deoxynucleotides or ribonucleotides or precursors thereof covalently linked or linked via a spacer to a non-radioactive labelling group wherein said labeling group is linked to the nucleobase of said nucleoside or nucleotide or precursor thereof.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: misc_feature
        ( B ) LOCATION: 17
        ( D ) OTHER INFORMATION: /note="C Fluorescein-labelled at 3'end"

( x i ) SEQUENCE DESCRIPTION: SEQ ID NO:1:

CAGGAAACAG CTATAGC                                                                                          17

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: misc_feature
        ( B ) LOCATION: 17
        ( D ) OTHER INFORMATION: /note="C Fluorescein-labelled at 3'end"

( x i ) SEQUENCE DESCRIPTION: SEQ ID NO:2:

CAGTATCGAC AAAGGAC                                                                                          17

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: misc_feature
        ( B ) LOCATION: 1
        ( D ) OTHER INFORMATION: /note="A Fluorescein-labelled at 3'end"

( x i ) SEQUENCE DESCRIPTION: SEQ ID NO:3:

TTTCACACAG GAAACAGCTA TGA                                                                                   23

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: misc_feature
        ( B ) LOCATION: 17
        ( D ) OTHER INFORMATION: /note="A Fluorescein-labelled at 3'end"

( x i ) SEQUENCE DESCRIPTION: SEQ ID NO:4:

TTGTAAAACG ACGGCCA                                                                                          17

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:

(A) NAME/KEY: misc_feature
(B) LOCATION: 17
(D) OTHER INFORMATION: /note="C Fluorescein-labelled at 3'end"

(xi) SEQUENCE DESCRIPTION: SEQ ID NO:5:

AAAACGACGG CCAGTGC 17